US00PP35894P2

(12) United States Plant Patent
Contreras

(10) Patent No.: US PP35,894 P2
(45) Date of Patent: Jul. 2, 2024

(54) ***VACCINIUM OVATUM* PLANT NAMED 'CASCADE JEWEL'**

(50) Latin Name: *Vaccinium ovatum*
Varietal Denomination: Cascade Jewel

(71) Applicant: Oregon State University, Corvallis, OR (US)

(72) Inventor: Ryan N. Contreras, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 18/214,058

(22) Filed: Jun. 26, 2023

(51) Int. Cl.
*A01H 5/00* (2018.01)
*A01H 6/36* (2018.01)

(52) U.S. Cl.
USPC ..... Plt./156

(58) Field of Classification Search
USPC ..... Plt./157, 156
See application file for complete search history.

*Primary Examiner* — Karen M Redden
(74) *Attorney, Agent, or Firm* — Klarquist Sparkman, LLP

(57) ABSTRACT

A new *Vaccinium ovatum* plant distinguished by its upright and vigorous, yet compact growth habit, dense branching, and DNA content (tetraploid).

3 Drawing Sheets

Latin name of the genus and species of the plant claimed: *Vaccinium ovatum.*

Variety denomination: 'Cascade Jewel'.

BACKGROUND

The present application relates to a new and distinct ornamental variety of *Vaccinium ovatum* named 'Cascade Jewel'. 'Cascade Jewel' is a tetraploid selection of *Vaccinium ovatum* with a DNA content of 2.52 pg. In comparison, diploid seedlings have a mean DNA content of 1.22 pg. Tetraploidy was induced by chemical treatment of seed (as described in Neill and Contreras, *HortScience,* 57(2), 312-318, 2022) collected from an unpatented seedling of unknown parentage growing in a cultivated area in Corvallis, Oregon in 2012-2013. 'Cascade Jewel' was among a group of diploids, mixoploids (cytochimeras), and tetraploids, that were evaluated between 2014-2020. 'Cascade Jewel', which was originally accessioned and tested as 12-0018-124, was selected as superior in 2017 due to its growth habit. It has continued to stand out as being vigorous and more amenable to commercial nursery production than other genotypes of all cytotypes. It has performed well in micropropagation and production trials, and is superior to wild-type plants due to its compact, but upright and densely branched growth habit and vigor.

SUMMARY

Plants of the new *Vaccinium ovatum* have not been observed under all possible combinations of environmental conditions and cultural practices. However, the following traits have been consistently observed and are a unique combination of characteristics for 'Cascade Jewel':

1. DNA content consistent with tetraploidy (2.52 pg)
2. Upright and vigorous, yet compact growth
3. Dense branching Diploid seedlings evaluated at the same time had an average height and width of 44 cm×53 cm compared to 28 cm×41 cm for 'Cascade Jewel' during the 2017-2018 growing season, thus 'Cascade Jewel' is at least more compact than diploids when immature, however, diploids were not maintained to determine whether 'Cascade Jewel' remains more compact at maturity.

Asexual reproduction of this new variety by vegetative cuttings and micropropagation shows that the foregoing characteristics come true to form, are firmly fixed, and are established and transmitted through succeeding propagations.

Certain characteristics of this variety may change with changing environmental conditions (such as photoperiod, temperature, moisture, soil conditions, nutrient availability, or other factors). Thus, the phenotype may vary somewhat with variations in environmental conditions without any variance in genotype, including ploidy level. Color designations (hue/value/chroma) are made with reference to The *Royal Horticultural Society Colour Chart* (R.H.S.) $6^{th}$ edition, 2015.

Figure 1:
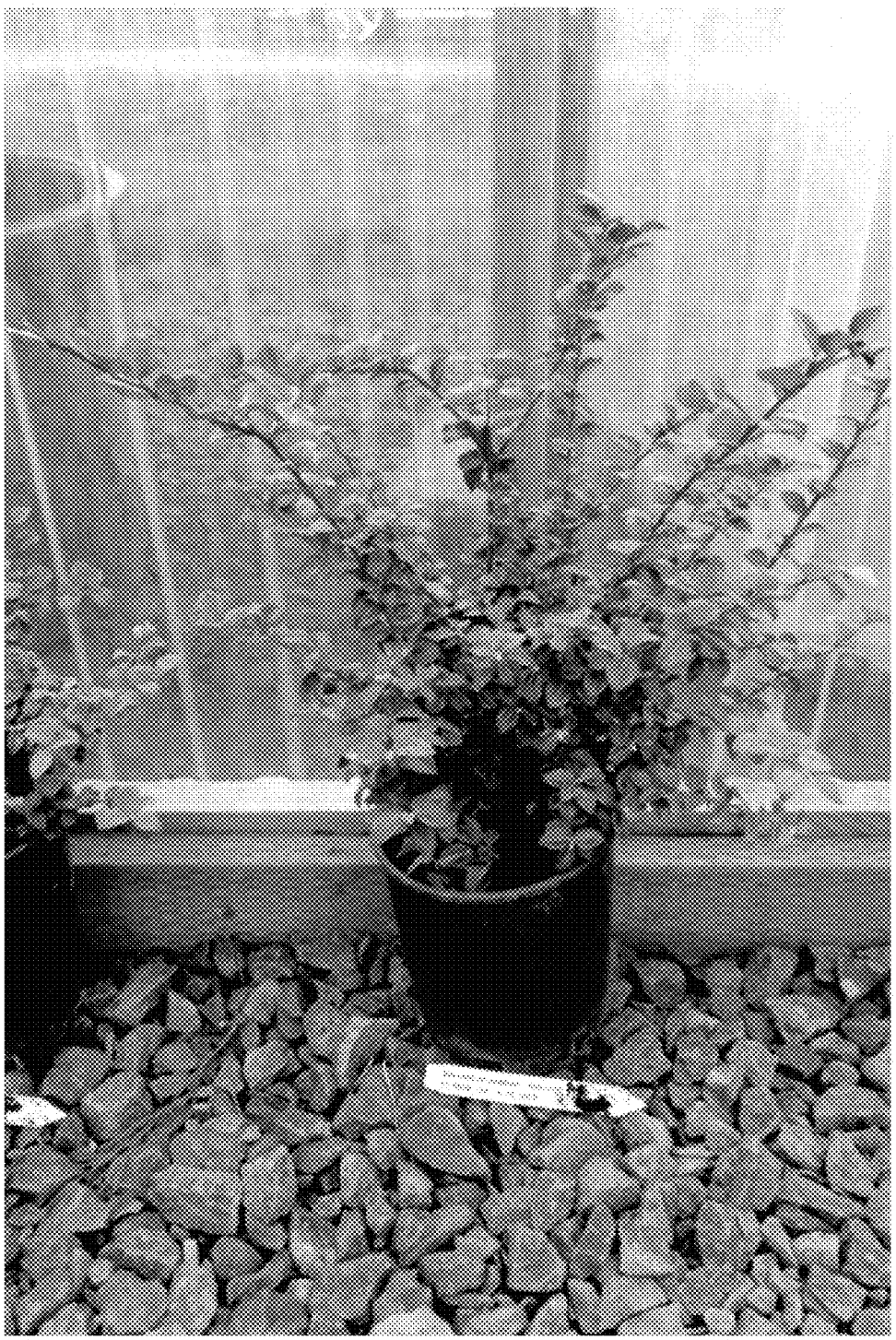
FIG. 1 is a photograph showing a side perspective of an unpruned container-grown plant of the original selection of 'Cascade Jewel' grown in an outdoor nursery. The photo was taken on Feb. 2, 2021.
Figure 2:
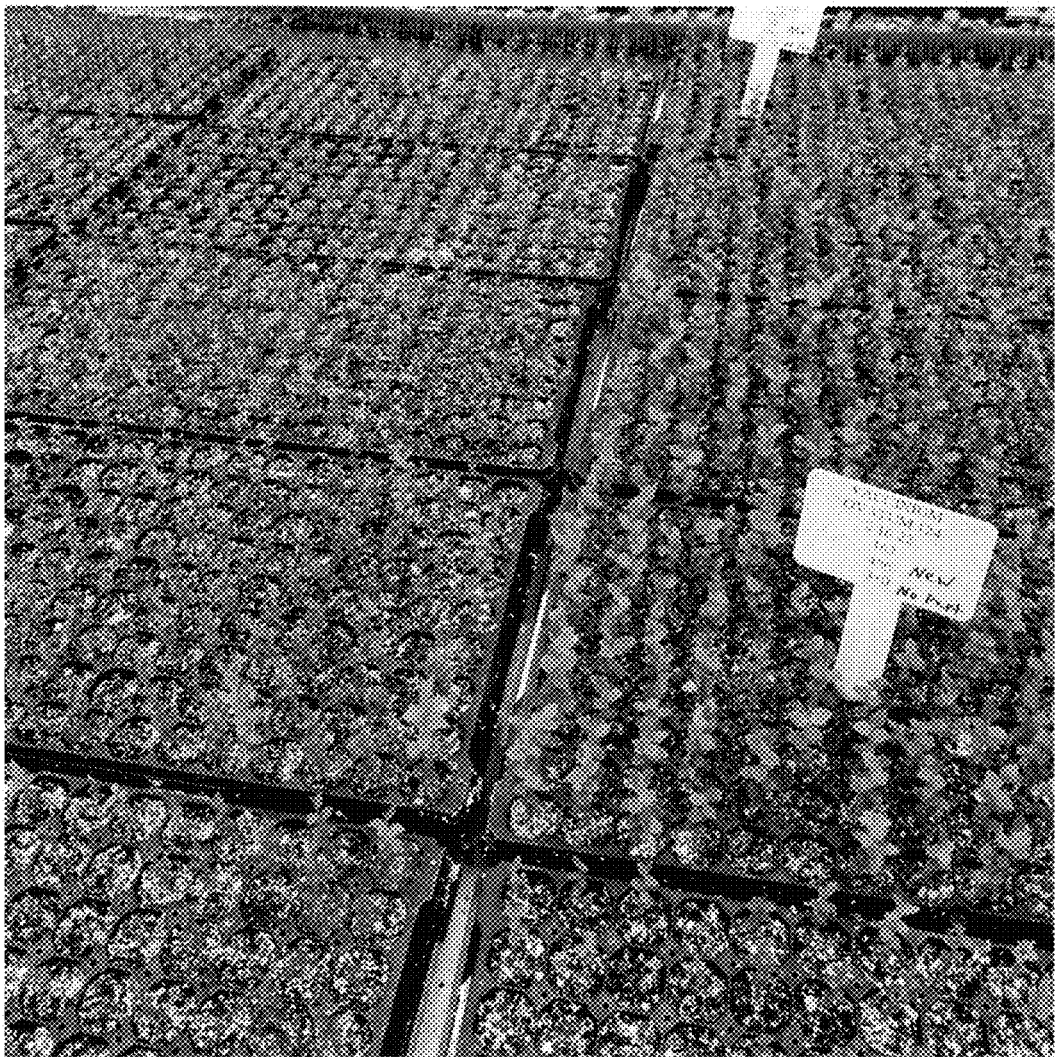
FIG. 2 is a photograph showing the superior performance of 'Cascade Jewel' plants produced in tissue culture (right) as compared to plants of a different genotype that are the same age (left). The photo was taken on Jun. 7, 2022.
Figure 3:
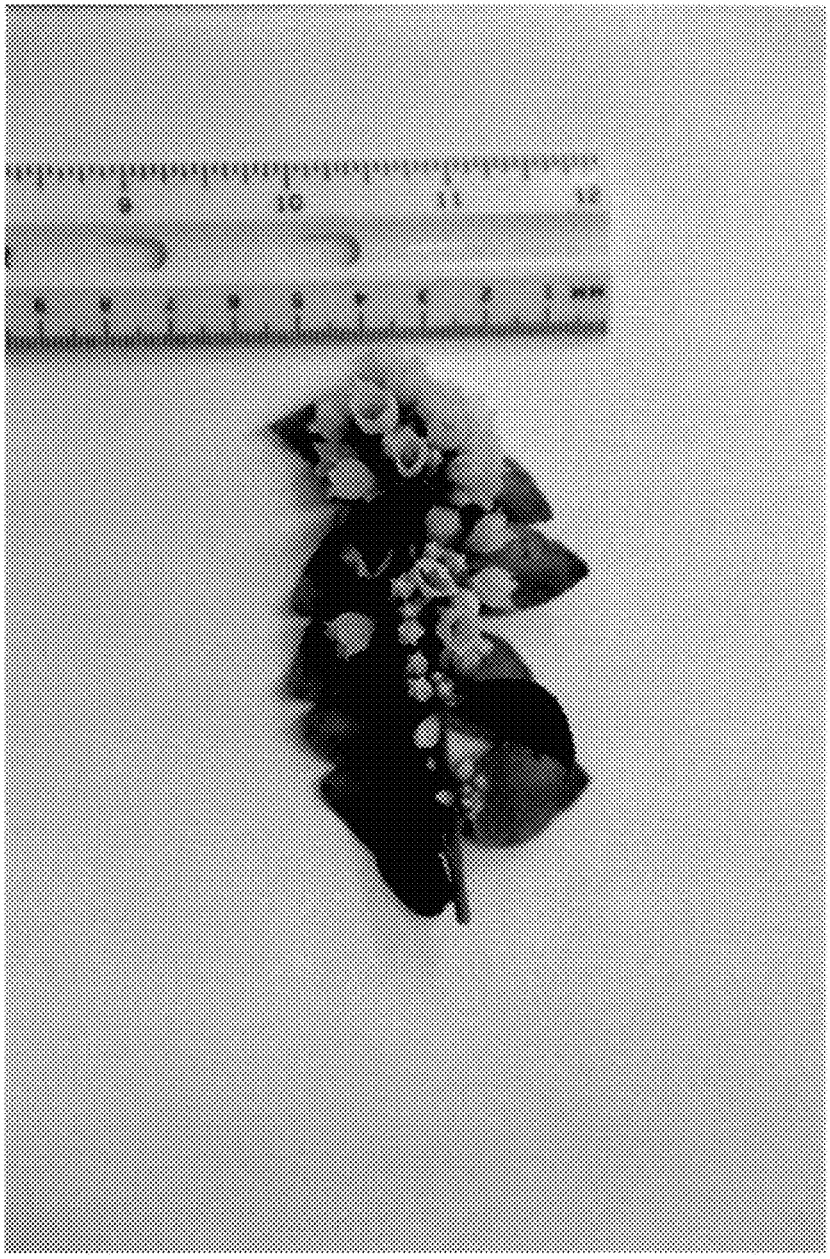
FIG. 3 is a photograph of a branch of 'Cascade Jewel' illustrating clusters of campanulate flowers produced in the axils of the seven terminal nodes. The branch was collected from a plant that was greenhouse forced to induce flowering. The photo was taken in February 2023.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED BOTANICAL DESCRIPTION

The following is a detailed description while observing mature plants propagated from stem cuttings. Such plants ranged between two and five years of age and were found to have consistent morphology, apart from size (younger plants are smaller). Plants were propagated in protected environments then grown outdoors in partial shade in Corvallis, Oregon, USA. Flowering data was collected in late February, 2023, on plants that were induced to flower in a glasshouse.

Plant:

*Type*.—Evergreen shrub.

*Growth habit*.—Compact, dense, broadly upright.

*Height and spread*.—28 cm×41 cm tall and wide during the 2017-2018 growing season. Mature height and width are approximately 85 cm×100 cm.

*Hardiness*.—At least USDA Zone 7.

*Growth rate*.—Moderate.

*Propagation*.—Stem cuttings rooted at 95% and is amendable to tissue culture/micropropagation.

Stem:

*Stem shape*.—Round.

*Stem color*.—Last season stem RHS 183B, current season stem color RHS N34A, young stem color RHS 34B.

*Stem surface*.—Young stems are slightly glossy and becoming slightly puberulent.

*Internode length*.—5 mm to 15 mm with an average of 8.3 mm.

Leaves:

*Leaf length*.—27.9 mm (including petiole).

*Leaf width*.—15.9 mm.

*Shape*.—Ovate.

*Apex*.—Broadly acute.

*Base*.—Cordate.

*Margin*.—Crenate-serrate.

*Leaf surface*.—Smooth, slightly glossy.

*Venation pattern*.—Pinnate.

*Leaf blade length*.—24.4 mm.

*Leaf blade color*.—RHS 139A on mature adaxial surface; RHS 146A on mature abaxial surface. New foliage is RHS 179A on adaxial and abaxial surface.

*Leaf arrangement*.—Alternate, simple.

*Petiole*.—Color: RHS 176B at base of mature leaf, RHS 177A at distal end of mature leaf. Length: 3.5 mm.

Flowers:

*Inflorescence*.—Pendulous clusters of 6 to 17 (average of 10) flowers located in axils of terminal 5 to 9 nodes of stem.

*Bud*.—Shape: Oval. Length: 9 mm. Color: RHS N155C at base, RHS 62C at tip.

*Individual flower*.—Shape: Campanulate. Length: 1 cm (including corolla and ovary). Width: 7 mm. Aspect: Pendulous.

*Petals*.—Fused into a corolla.

*Corolla*.—Length: 8 mm. Width: 7 mm. Color: RHS NN155B (inside and outside). Corolla Lobe Length: 1 mm. Corolla Lobe Color: RHS 62C at tip.

*Stamen*.—Number: 10. Length: 5.4 mm. Width: 0.5 mm. Anther Color: RHS N167A at base, RHS 22A at terminal end. Pollen: Moderate. Pollen Color: RHS 158A.

*Pistil*.—Number: Average of 1. Style Length: 5.4 mm. Ovary Length: 2.5 mm. Ovary Width: 2.5 mm. Ovary Color: RHS 144A.

*Pedicel*.—Length: 6 mm. Diameter: 0.5 mm. Color: RHS 144A.

*Sepals*.—Shape: Ovate. Apex: Acute. Base: Fused at base. Margin: Entire. Number: 5. Length: 2.3 mm. Width: 1.7 mm. Color: RHS 151C on the upper and lower surfaces.

*Date of bloom*.—April to May.

*Lastingness of individual blooms*.—7 to 10 days.

*Flower fragrance*.—None.

Fruit:

*Size*.—7.95 mm diameter.

*Shape*.—Globose.

*Texture*.—Glossy, smooth, glabrous.

*Fruit use*.—Not grown for fruit production.

*Skin color*.—Immature 138B, maturing to 93A.

*Color of flesh*.—A blend between 194A to 194C.

*Seed*.—Oblong to oval, 30 per fruit, <1 mm in length and width, 171B in color.

Disease/pest resistance: No particular resistance has been observed.

I claim:

1. A new and distinct variety of *Vaccinium ovatum* plant named 'Cascade Jewel', substantially as illustrated and described herein.

* * * * *